United States Patent [19]

Odle

[11] Patent Number: 5,155,234

[45] Date of Patent: Oct. 13, 1992

[54] NITRATION OF PHTHALIC ACID AND PHTHALIC ANHYDRIDE USING NITRIC ACID

[75] Inventor: Roy R. Odle, Schuylerville, N.Y.

[73] Assignee: General Electric Company, Pittsfield, Mass.

[21] Appl. No.: 700,934

[22] Filed: May 13, 1991

Related U.S. Application Data

[63] Continuation of Ser. No. 488,410, Mar. 1, 1990, abandoned, which is a continuation of Ser. No. 170,701, Mar. 14, 1988, abandoned, which is a continuation of Ser. No. 559,575, Dec. 8, 1983, abandoned.

[51] Int. Cl.$^5$ .............................................. C07D 307/77
[52] U.S. Cl. .................... 549/243; 562/434; 562/856; 562/887
[58] Field of Search ...................... 562/434, 856, 887; 549/243

[56] References Cited

U.S. PATENT DOCUMENTS 3,981,933  9/1976  Cook et al. ......................... 568/934
4,902,809  2/1990  Groeneweg .
4,921,970  5/1990  Odle .

OTHER PUBLICATIONS

Hughes, et al., "Kinetics and Mechanism of Aromatic Nitration," Part II, pp. 2400–2440 (1949).
Noller, "Chemistry of Organic Compounds," pp. 439–455 (1957).

*Primary Examiner*—Michael L. Shippen
*Attorney, Agent, or Firm*—Mary A. Montebello

[57] ABSTRACT

A process for the preparation of nitrophthalic acid by the nitration of phthalic acid and/or phthalic anhydride using only nitric acid, said nitric acid having a concentration of at least about 95% by weight, and then recovering the nitrophthalic acid formed from the nitric acid solution.

11 Claims, No Drawings

NITRATION OF PHTHALIC ACID AND PHTHALIC ANHYDRIDE USING NITRIC ACID

This is a continuation of application Ser. No. 488,410, filed Mar. 1, 1990, now abandoned, which is a continuation of Ser. No. 170,701, filed Mar. 14, 1988, now abandoned, which is a continuation of Ser. No. 559,575, filed Dec. 8, 1983, now abandoned.

The present invention is concerned with an improved process for the nitration of phthalic acids and phthalic anhydrides. Specifically, the improved process of the present invention comprises forming a solution of the anhydride or acid in a solvent composed of at least about 95% by weight, preferably at least about 97% by weight, concentrated nitric acid within a temperature range of from about 20° C. to the boiling point of nitric acid, preferably from about 50° C. to the boiling point of nitric acid, most preferably from about 60° C. to about 85° C., allowing the nitration reaction to proceed to form the nitrated derivatives of the reactant and thereafter recovering such nitrated products by conventional recovery methods known in the art.

Alternative methods for preparing nitrated derivatives of aromatic compounds are continually being sought as many of these nitrated aromatic compounds are especially useful as starting reactants or intermediates in the preparation of commercial resinous compositions.

Cook et al (U.S. Pat. No. 3,981,933) disclose a process for the preparation of nitrated aromatic compounds having 6 to 18 carbon atoms, which process comprises contacting the aromatic compound, in the presence of methylene chloride as reaction medium, with from 80 to 100% by weight concentrated sulphuric acid and 90 to 100% by weight concentrated nitric acid, advantageously within a temperature range of from about −20° C. to about 50° C., or even somewhat higher, and thereafter isolating the nitro compound.

Bacha et al (U.S. Pat. No. 4,137,419) disclose a process for the preparation of 4-nitro-o-phthalic acid which involves nitrating an indene, polyindene, dihydronaphthalene or polydihydronaphthalene with concentrated nitric acid and thereafter oxidizing said nitrated organic compound with dilute nitric acid, said nitration being conducted with an aqueous nitric acid solution having a concentration of from about 70 to about 95 wt. % at a temperature of −40° C. to about 90° C. and said oxidation being conducted with an aqueous nitric acid solution having a concentration from about 5 to about 50 wt. % at a temperature of about 135° C. to about 210° C. Finally, Cook et al (U.S. Pat. No. 3,887,588) disclose a method for preparing nitrophthalic anhydrides by treating phthalic anhydride in concentrated sulphuric acid with concentrated nitric acid and thereafter extracting the formed nitrophthalic anhydrides with methylene chloride.

SUMMARY

Unexpectedly, it is now been discovered that phthalic acid and phthalic anhydride may be nitrated to form a mixture of 3- and 4- nitrophthalic acid in a nitration process which employs only nitric acid. Specifically, the process of the present invention comprises 1) mixing the phthalic acid or phthalic anhydride with at least about 95% by weight, preferably at least about 97% by weight concentrated nitric acid; 2) reacting the mixture within a temperature range of from about 20° C. to the boiling point of nitric acid, preferably from about 50° C. to the boiling point of nitric acid, most preferably from about 60° C. to about 85° C.; 3) allowing the reaction to run to produce the nitrated derivatives and 4) thereafter recovering the nitrated products by known methods to obtain a mixture composed essentially of the 3- and 4- isomers of nitrophthalic acid. The weight ratio of the starting reactants, nitric acid to phthalic acid or phthalic anhydride may vary widely. Generally said ratio is from about 0.4 to about 50, preferably from about 5 to about 30, most preferably from about 9 to about 15.

The process of the present invention eliminates the additional requirement and expense of sulfuric acid, is effective over a wide range of temperatures and provides excellent yields. Furthermore, this new process is considered safer and less costly than prior processes, particularly in the event of a cooling failure and/or a runaway reaction. Finally, recovery of the reaction products of the present invention may be by any known method for recovery of nitrated products including drying, evaporation, extraction and the like and is easier since removal of sulfuric acid is no longer a consideration. Rather, the products of the present invention are recovered directly from the nitric acid.

DETAILED DESCRIPTION OF THE INVENTION

For the purpose of this specification and the appended claims, the "boiling point of nitric acid" is defined as the temperature at which the specific nitric acid used, under the pressure employed, boils. This definition is necessitated by the fact that nitric acids of less then 100% concentration have a higher boiling point than 100% concentrated nitric acid and that the boiling point of nitric acid may be elevated by raising the pressure under which the reaction takes place above atmosphere. Such instances are clearly intended to be within the full scope of the present invention as set forth in this specification and claimed by the appended claims.

The nitric acid useful for the nitration process disclosed herein should have a concentration of at least about 95% by weight and is preferably within the range of from about 97 to about 100% concentration by weight. Nitric acids of lower concentration are useful for the all nitric acid nitration process; however, the use of such concentrations results in processes which are too slow to be cost effective. Nitric acids of such concentrations are available commercially or may be prepared by known concentrating methods from more widely available commerical nitric acid of 60 to 67% concentration.

The amount of concentrated nitric acid used should be at least of the stoichiometric amount necessary to attach one nitro ($NO_2$) group on the aromatic nucleus of the phthalic acid or phthalic anhydride. Generally, the weight ratio of nitric acid to the phthalic acid or phthalic anhydride should be from about 0.4 to about 50, preferably from about 5 to about 30, most preferably from about 9 to about 15. Obviously, lower or higher amounts of nitric acid may be used in the process of the present invention, however, lower amounts of nitric acid result in poor yields and too slow a reaction rate as to be cost effective, whereas higher amounts of nitric acid may result in unnecessary spoiling of concentrated nitric acid and increased cost for such acid and its recycling.

Phthalic acids and phthalic anhydrides useful in the present invention are well known and widely available commercially. Sources for these materials include Mallinckrodt, Inc. of St. Louis, Mo.; Monsanto Company, of St. Louis, Mo.; and Exxon Chemical of Houston, Tex. Further, it is to be understood that phthalic acid and phthalic anhydride include substituted derivatives thereof wherein the aromatic ring of the acid or anhydride is substituted with one or more alkyl radicals having 1 to 10, preferably 1 to 4 carbon atoms and/or one or more halogen atoms, as well as functional derivatives thereof including the diacids, dianhydrides, acid anhydrides, acid halides and other halo derivatives thereof, for example trimelletic acid, pyromelletic acid, trimelletic acid anhydride, pyromelletic dianhdyride, phthalylchloride and the like.

The process of the present invention comprises mixing together the concentrated nitric acid and the phthalic acid or phthalic anhydride in a reactor or reactors equipped with a stirrer or agitating means and means for heating or cooling the reactor(s). The reactor(s) may be such as to allow for either batch or continuous processing.

Specific variations in the design of the process systems employable to practice the present invention are known to those skilled in the art. For example, it is possible to use one or more reactors in series or in parallel which operate in the plug flow mode with or without radial mixing and with or without heating or cooling. Alternatively, it is possible to use one or more reactors in series or in parallel which operate in the back mixing mode, again with or without heating and cooling and operating in a batch or continuous mode. Finally, it is also possible to use a combination of reactors with features of both the foregoing.

The mode of mixing and sequence of addition of reactants is not critical to the present invention. Feed of the reactants may either be into the first reactor or be portioned among the reactors if more than one reactor is used, or they may be entered at different locations of the reactor or reactors. Further, the reactants may be pre-mixed before entering the reaction process or they may be fed separately. It is also possible that one or both reactants are brought to the desired reaction temperature prior to mixing or entering the reactor.

The pressure range under which this process operates may vary from vacuum to above atmospheric pressure. Depending on the type of reactor or reactors employed, they may preferentially operate under slight vacuum for process and safety reasons. Otherwise, the process is generally run at about atmospheric pressure.

Generally, the reaction temperature should fall within the range of from about 20° C. to the boiling point of nitric acid, preferably from about 50° C. to the boiling point of nitric acid, most preferably from about 60° C. to about 85° C. The actual temperature to be employed is dependent upon the desired rate of reaction and the economics of the nitration. More specifically, the higher the temperature the faster the nitration reaction. However, very high temperatures, around the boiling point of nitric acid, should be avoided to prevent the loss of nitric acid due to both boiling and conversion to nitrous oxides.

It should also be noted that temperatures outside the range of temperatures disclosed above may be employed with the present process. However, lower temperatures result in a reaction rate which is too slow to be cost effective, whereas higher temperatures require operation at above atmospheric pressure to prevent boiling and subsequent loss of nitric acid.

While the temperature at which the reaction is run has the most significant impact on reaction rate, the specific reactants used and the ratio of reactants in the reaction mix also influence the reaction rate and isomer ratio. With respect to the former, the higher the concentration of the nitric acid in the initial mix or as added during continuous processing the faster the reaction rate. Finally, with respect to the ratio of the reactant mix, it is found that the rate of reaction increases as the weight ratio of nitric acid to phthalic acid or phthalic anhydride increases. Also, as the weight ratio increases, the ratio of 4- isomer to 3- isomer in the reaction products decreases, i.e. approaches 1:1.

Thus by varying any one or all of the foregoing, one may significantly increase or decrease the time for which the reaction should run to obtain optimum yield. In general, with a reaction run at a temperature within the preferred range, e.g. 60°-85° C., up to about 90% or greater yields may be obtained within three hours. Optionally, these yields may be increased further by allowing the reaction mix to stand for a period of time prior to separation.

As noted above, the pressure under which the reaction is run should generally be about atmospheric pressure. It is possible, though, to vary the reactor pressures. This would be expected to have only minor influence on the reaction rate at the same temperature. However, an increase of both pressure and temperature would be expected to enhance the reaction rate measurably. Thus, as noted above, since the boiling point of nitric acid may be elevated by increasing the pressure in the reaction vessel, such elevated boiling points are intended to be within the full scope of the term "about the boiling point of nitric acid" in the specification and appended claims.

The desired reaction products of the process of the present invention are comprised primarily of the 3- and 4- isomers of nitrophthalic acid. Generally, said ratio varies from about a 1:1 mix to about a 3:2 mix of the 4- isomer to 3- isomer.

The reaction products themselves may be recovered from the reaction mix by any of the known methods for recovery of nitrated products. Exemplary of the methods available include: extraction; evaporation; drying; precipitation and drying and the like. Recovered unreacted phthalic acid and/or phthalic anhydride may be reused and the spoiled or used nitric acid may be recycled by known methods for reuse.

In order that those skilled in the art may better understand how the present invention may be practiced, the following examples are given by way of illustration and not by way of limitation.

DESCRIPTION OF THE PREFERRED EMBODIMENTS

Generally, the reaction products were analyzed by High Pressure Liquid Chromatography (HPLC) wherein 50 $\mu$l aliquots were quenched into 3.8 mls of a solution comprising 0.5M tetraethylammonium bromide and 0.96M sodium acetate. The samples were analyzed at 280 nm on a Waters $\mu$ Bondpak/$C_{18}$ column using 1.5 ml/min of mobile phase which consisted of a solution of 0.005M tetraethylammonium bromide, 0.035M acetic acid and 0.070M sodium acetate.

EXAMPLES 1 AND 2

100 parts by weight and 150 parts by weight 99% by weight concentrated nitric acid are each added to a reaction vessel and brought to a temperature of 70° C. To each solution is added 10 parts by weight phthalic acid. Nitration is allowed to continue at 70° C. for three hours and produces yields of greater than 90% of theoretical yield consisting essentially of a mixture of 3- and 4- nitrophthalic acid. Table 1 shows the make-up of the reaction product mix in mole percent. The mole ratio of 4- to 3- nitrophthalic acid formed was approximately 1.1:1.

TABLE 1

| | Wt. HNO$_3$/ wt. Phthalic Acid | Reaction Product Mix (Mole %) 3- and 4-NP Acid | Phthalic Acid |
|---|---|---|---|
| Example 1 | 10/1 | 96.0 | 3.98 |
| Example 2 | 15/1 | 94.4 | 5.62 |

EXAMPLES 3-16

A series of experiments are run as in Examples 1 and 2 except that phthalic anhydride is substituted for phthalic acid. The temperature and weight ratio of the reactions are as presented in Table 2. Table 2 also presents the mole % based on the theoretical yield of the products formed during a 3 hour nitration.

TABLE 2

| Example | Temperature | Wt. HNO$_3$/ wt. Phthalic Anhydride | 4- and 3- Nitrophthalic Acid |
|---|---|---|---|
| 3 | 25 | 5/1 | 12.8 (25.6)$^a$ |
| 4 | 25 | 10/1 | 18.6 (38.2)$^a$ |
| 5 | 25 | 15/1 | 21.6 (43.3)$^a$ |
| 6 | 25 | 20/1 | 23.7 (46.0)$^a$ |
| 7 | 50 | 5/1 | 52.5 |
| 8 | 50 | 10/1 | 68.3 |
| 9 | 50 | 15/1 | 75.2 |
| 10 | 50 | 20/1 | 77.6 |
| 11 | 70 | 10/1 | 93.5 |
| 12 | 70 | 15/1 | 88.0 |
| 13 | 80 | 5/1 | 94.7 |
| 14 | 80 | 10/1 | 99.1 |
| 15 | 80 | 15/1 | 100 |
| 16 | 80 | 20/1 | 100 |

$^a$Number in parenthesis represent mole % formed after 7 hours.

Table 2 demonstrates the ability of the all nitric nitration process to be run at various temperatures and weight ratio of starting reactants. It is clear that the higher temperatures are preferred. It is further evident that higher mole ratios of nitric acid to phthalic anhydride favors a faster reaction rate.

EXAMPLES 17-19

100 parts by weight of 99, 97 and 95% concentrated nitric acid were each added to a reaction vessel and brought to 70° C. To each of these is added 10 parts by weight phthalic anhydride. The nitration reaction is allowed to proceed for 3 hours after which the reaction products comprising the 3- and 4-isomers of nitrophthalic acid and unreacted phthalic acid, as shown in Table 3 in mole percent, are recovered.

TABLE 3

| Example | HNO$_3$ | 3- and 4- Nitrophthalic Acid | Phthalic Acid |
|---|---|---|---|
| 17 | 99 | 93.1 | 6.9 |
| 18 | 97 | 83.5 | 16.5 |
| 19 | 95 | 70.2 | 29.8 |

From Table 3, it is clear that the concentration of the nitric acid greatly influences the reaction rate.

Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. A process for the nitration of phthalic acid substrates consisting of forming a solution of phthalic acid substrate selected from the group consisting of
   i) phthalic acid
   ii) phthalic anhydride,
   iii) halo and $C_1$ to $C_{10}$ alkyl substituted derivatives of (i) and (ii), and
   iv) diacid, acid anhydride and acid halide functional derivatives of (i), (ii) and (iii), with a nitrating reagent consisting essentially of nitric acid, said nitric acid being of at least about 95% concentration, allowing the mixture to react at a temperature of from about 20° C. to about the boiling point of the nitric acid and thereafter recovering the nitrated products, said nitrated products being essentially free from poly-nitrated products.

2. The process of claim 1 wherein the phthalic acid substrate is selected from the group consisting of phthalic acid and phthalic anhydride.

3. The process of claim 1 or 2 wherein the temperature at which the nitration reaction is allowed to proceed is from about 50° C. to the boiling point of nitric acid.

4. The process of claim 1 or 2 wherein the temperature at which the nitration reaction is allowed to proceed is from about 60° C. to about 85° C.

5. The process of claim 1 or 2 wherein the weight ratio of nitric acid to substrate is from about 0.4 to about 50.

6. The process of claim 1 or 2 wherein the weight ratio of nitric acid to substrate is from about 5 to about 20.

7. The process of claim 1 or 2 wherein the weight ratio of nitric acid to substrate is from about 9 to about 15.

8. The process of claim 1 or 2 wherein the nitric acid is at least about 97% by weight concentration.

9. The process of claim 1 or 2 wherein the nitric acid is at least about 99% by weight concentration.

10. The process of claim 2 wherein the substrate is phthalic acid.

11. The process of claim 2 wherein the substrate is phthalic anhydride.

* * * * *